(12) United States Patent
Wallace et al.

(10) Patent No.: US 6,527,780 B1
(45) Date of Patent: Mar. 4, 2003

(54) MEDICAL IMPLANT INSERTION SYSTEM

(75) Inventors: Raymond G. Wallace, Memphis, TN (US); Gary A. Tatge, Memphis, TN (US)

(73) Assignee: Odyssey Medical, Inc., Memphis, TN (US)

( * ) Notice: Subject to any disclaimer, the term of this patent is extended or adjusted under 35 U.S.C. 154(b) by 150 days.

(21) Appl. No.: 09/703,103

(22) Filed: Oct. 31, 2000

(51) Int. Cl.$^7$ ................................................ A61F 11/00
(52) U.S. Cl. ........................................ 606/108; 606/1
(58) Field of Search ........................ 606/1, 108, 109; 604/8, 294

(56) References Cited

U.S. PATENT DOCUMENTS

| | | | |
|---|---|---|---|
| 3,888,258 A | 6/1975 | Akiyama | 128/305 |
| 3,897,786 A | 8/1975 | Garnett et al. | 128/303 R |
| 3,913,584 A | 10/1975 | Walchle et al. | 128/305 |
| 4,065,816 A * | 1/1978 | Sawyer | 606/108 |
| 4,473,073 A | 9/1984 | Darnell | 128/303 |
| 4,968,296 A * | 11/1990 | Ritch et al. | 604/8 |
| 5,053,040 A * | 10/1991 | Goldsmith, III | 606/109 |
| 5,172,701 A | 12/1992 | Leigh | 128/753 |
| 5,496,329 A * | 3/1996 | Reisinger | 606/108 |
| 5,643,280 A * | 7/1997 | Del Rio et al. | 606/109 |
| 5,681,323 A | 10/1997 | Arick | 606/108 |
| 5,741,292 A | 4/1998 | Mendius | 606/191 |
| 5,830,171 A | 11/1998 | Wallace | 604/8 |
| 5,868,697 A | 2/1999 | Richter et al. | 604/8 |
| 6,183,467 B1 * | 2/2001 | Shapeton et al. | 606/1 |
| 6,344,047 B1 * | 2/2002 | Price et al. | 604/298 |

* cited by examiner

*Primary Examiner*—Rodney M. Lindsey
(74) *Attorney, Agent, or Firm*—Walker, McKenzie & Walker PC

(57) ABSTRACT

A medical implant insertion system comprising a medical implant cartridge including a medical implant, a head having a first end and a second end, and a pin slidably extending through the head, the pin having a first end and a second end, the first end of the pin being located adjacent the first end of the head and being removably attached to the medical implant; the second end of the pin being positioned adjacent the second end of the head; and a medical implant insertion instrument including a handle for removable attachment to the second end of the head of the medical implant cartridge, collet structure for attachment to the second end of the pin of the medical implant cartridge when the handle is attached to the second end of the head of the medical implant cartridge, and actuator structure;for causing the medical implant to detach from the pin of the medical implant cartridge.

11 Claims, 5 Drawing Sheets

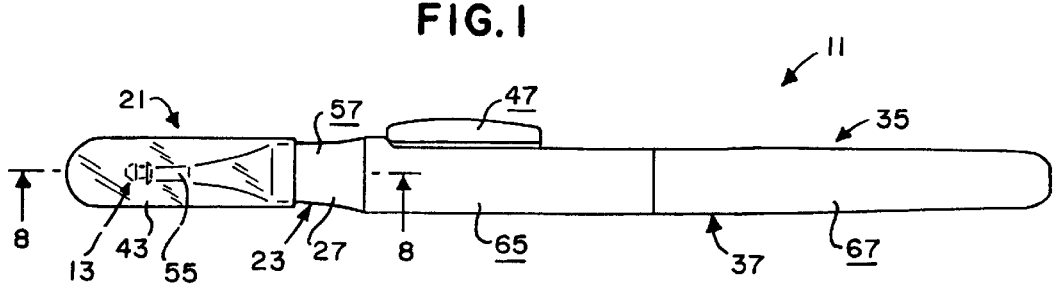
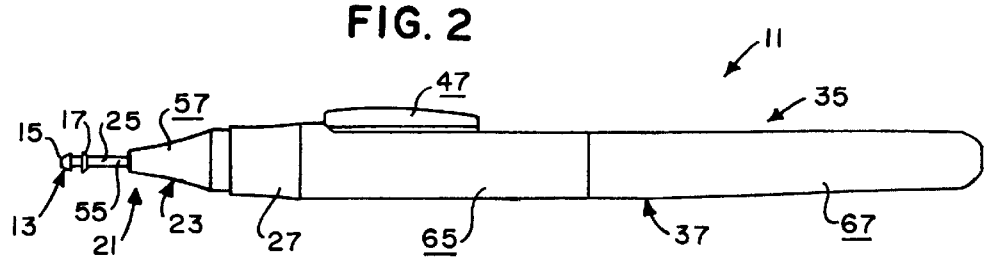
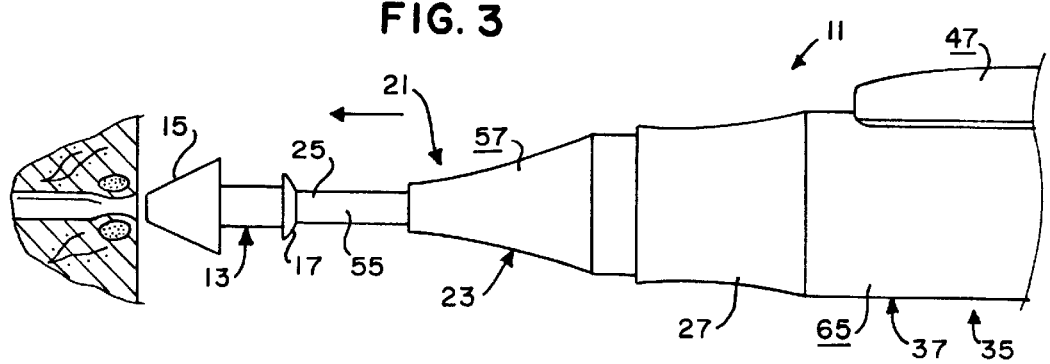
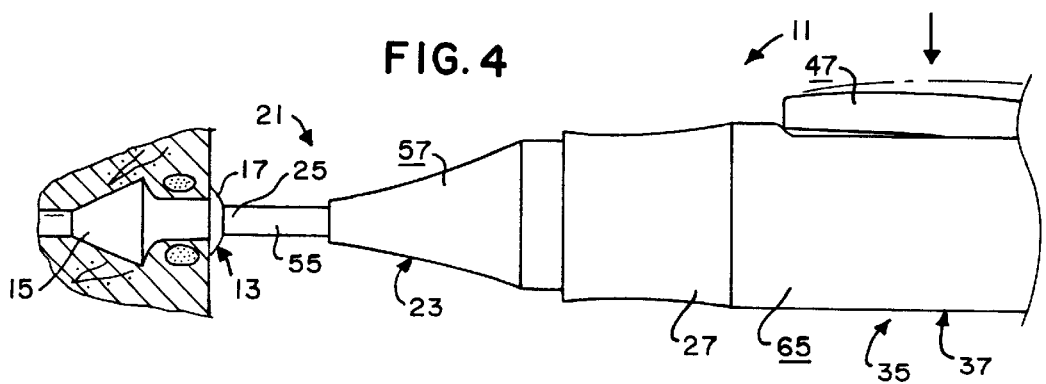

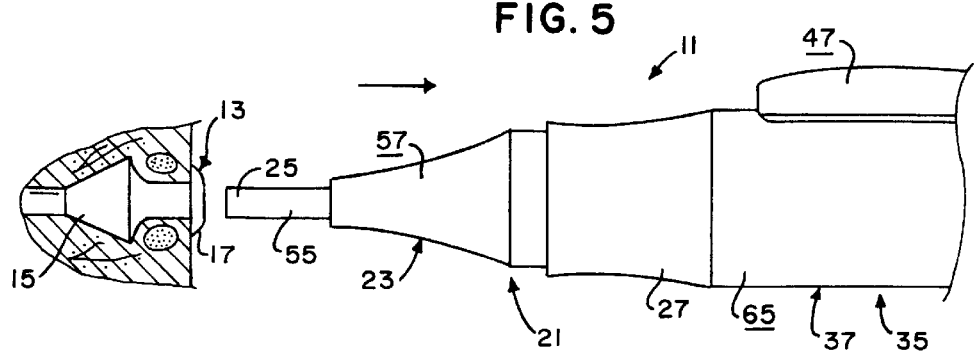
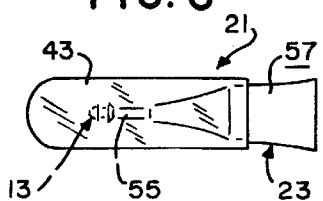
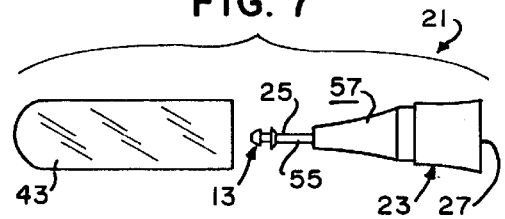
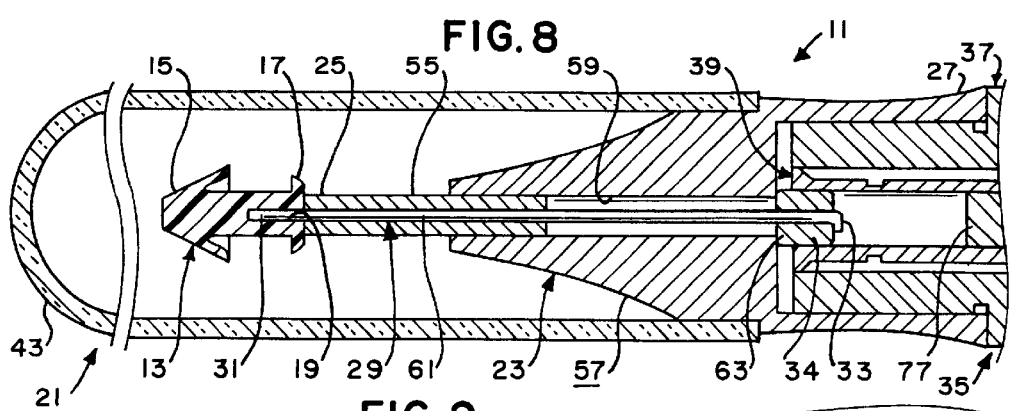
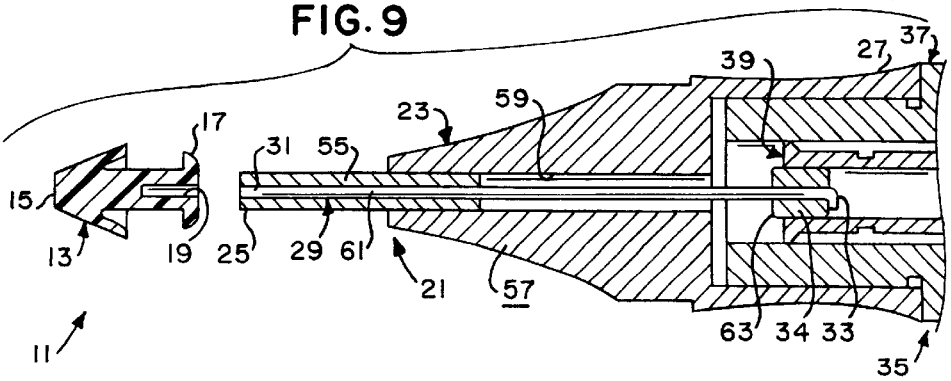

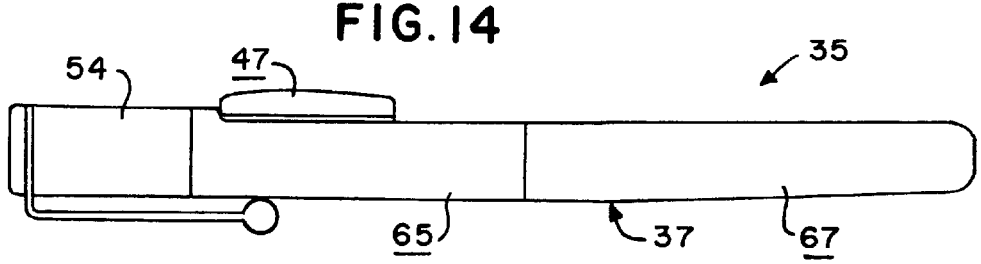
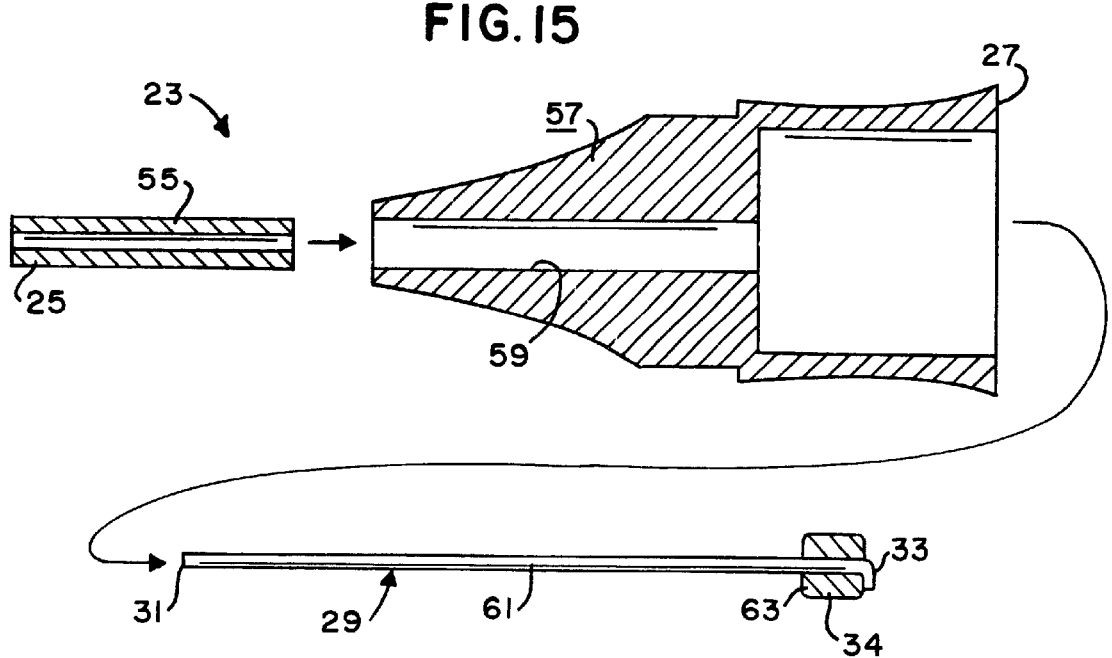

MEDICAL IMPLANT INSERTION SYSTEM

CROSS-REFERENCE TO RELATED APPLICATIONS

Not Applicable.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates, in general, to medical implants such as punctal occluders or the like, and, more specifically, to systems including both medical implants and medical implant insertion instruments.

2. Information Disclosure Statement

Various small medical implants such as myringotomy tubes, punctal occluders (punctum plugs), and the like are often sold pre-loaded on disposable insertion instruments as a sterile unit or kit. Such practices save implantation time and insure that the implants are offered for implantation in a sterile condition.

Punctal occlusion is becoming the most accepted clinical treatment for dry eye and related conditions. Today, all known suppliers of punctal occluders (punctum plugs) sell their plugs pre-loaded on insertion instruments as a sterile unit or kit (one sterile insertion instrument per sterile punctum plug). When the insertion of the plug is complete, the entire insertion instrument is immediately discarded. Unfortunately, this results in the majority of the purchase price of the punctum plug kit being discarded. This wasteful disposal of the entire insertion instrument has resulted in an artificially high delivery cost of punctal occlusion, a very inefficient use of valuable resources and a very unfortunate contribution to non-degradable waste in our environment.

A preliminary patentability search conducted in class 606, subclasses 108, 109, 185 and 191 produced the following patents which appear to be relevant to the present invention:

Akiyama, U.S. Pat. No. 3,888,258, issued Jun. 10, 1975, discloses an apparatus for introducing a drain for the eardrum.

Garnett et al., U.S. Pat. No. 3,897,786, issued Aug. 5, 1975, discloses a disposable apparatus for inserting a myringotomy tube.

Walchle et al., U.S. Pat. No. 3,913,584, issued Oct. 21, 1975, discloses an otological vent tube inserter.

Darnell, U.S. Pat. No. 4,473,073, issued Sep. 25, 1984, discloses a myringotomy tube inserter.

Leigh, U.S. Pat. No. 5,172,701, issued Dec. 22, 1992, discloses a single use biopsy device.

Arick, U.S. Pat. No. 5,681,323, issued Oct. 28, 1997, discloses a cricothyrotomy. tube insertion device.

Mendius, U.S. Pat. No. 5,741,292, issued Apr. 21, 1998, discloses a punctum plug inserting instrument.

Wallace, U.S. Pat. No. 5,830,171, issued Nov. 3, 1998, discloses a punctal occluder.

Richter et al., U.S. Pat. No. 5,868,697, issued Feb. 9, 1999, discloses an intraocular implant and delivery device.

Nothing in the known prior art discloses or suggests the present invention. More specifically, nothing in the known prior art discloses or suggests a medical implant insertion system with a medical implant cartridge including a medical implant, a head having a first end and a second end, and a pin slidably extending through the head, the pin having a first end and a second end, the first end of the pin being located adjacent the first end of the head and being removably attached to the medical implant; the second end of the pin being positioned adjacent the second end of the head; and with a medical implant insertion instrument including a handle for removable attachment to the second end of the head of the medical implant cartridge, collet means for attachment to the second end of the pin of the medical implant cartridge when the handle is attached to the second end of the head of the medical implant cartridge, and actuator means for causing the medical implant to detach from the pin of the medical implant cartridge.

BRIEF SUMMARY OF THE INVENTION

The present invention provides a medical implant insertion system. A basic concept of the present invention is to provide a medical implant insertion system that consist, in general, of two components, a high quality reusable insertion instrument and a sterile, single use, pre-loaded cartridge.

The medical implant insertion system of the present invention comprises, in general, a medical implant cartridge including a medical implant, a head having a first end and a second end, and a pin slidably extending through the head, the pin having a first end located adjacent the first end of the head and removably attached to the medical implant, and having a second end positioned adjacent the second end of the head; and a medical implant insertion instrument including a handle for removable attachment to the second end of the head of the medical implant cartridge, collet means for attachment to the second end of the pin of the medical implant cartridge when the handle is attached to the second end of the head of the medical implant cartridge, and actuator means for causing the medical implant to detach from the pin of the medical implant cartridge.

One object of the present invention is to provide an economical, yet precise system for the delivery punctal occluders and the like.

BRIEF DESCRIPTION OF THE SEVERAL VIEWS OF THE DRAWINGS

FIG. 1 is a side elevational view of the medical implant insertion system of the present invention.

FIG. 2 is a side elevational view similar to FIG. 1 but showing the medical implant of the medical implant insertion system of the present invention exposed and ready for implanting.

FIG. 3 is an enlarged view of a portion of FIG. 2, showing an initial step of the implantation of the medical implant.

FIG. 4 is a view similar to FIG. 3 but showing the medical implant fully implanted and being released from the medical implant insertion instrument of the medical implant insertion system of the present invention.

FIG. 5 is a view similar to FIGS. 3 and 4 but showing the medical implant insertion instrument of the medical implant insertion system of the present invention fully separated from and being pulled away from the medical implant.

FIG. 6 is a side elevational view of a medical implant cartridge of the medical implant insertion system of the present invention.

FIG. 7 is a exploded view of the medical implant cartridge, showing a removable cap thereof separated from remainder thereof.

FIG. 8 is a sectional view substantially as taken on line 8—8 of FIG. 1 on an enlarged scale and with portions thereof broken away for clarity.

FIG. 9 is a sectional view similar to FIG. 9 but showing the medical implant and the medical implant insertion instrument of the medical implant insertion system of the present invention separated from one another.

FIG. 14 is a front elevational view of the medical implant insertion instrument of the medical implant insertion system of the present invention, shown with a protective cap thereon.

FIG. 15 is an exploded view of the head and pin of the medical implant cartridge of the medical implant insertion system of the present invention, with parts thereof shown in section for clarity.

DETAILED DESCRIPTION OF THE INVENTION

Figure 10:
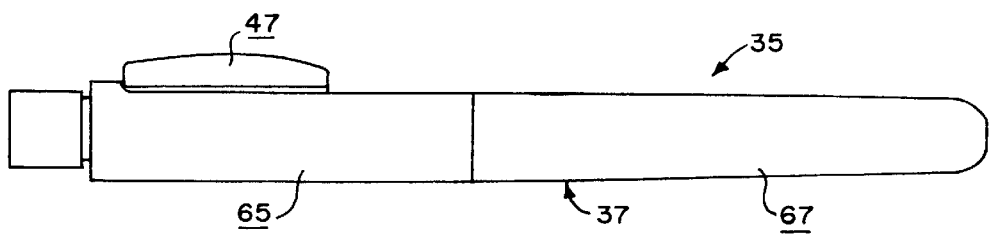
FIG. 10 is a front elevational view of the medical implant insertion instrument of the medical implant insertion system of the present invention.
Figure 11:
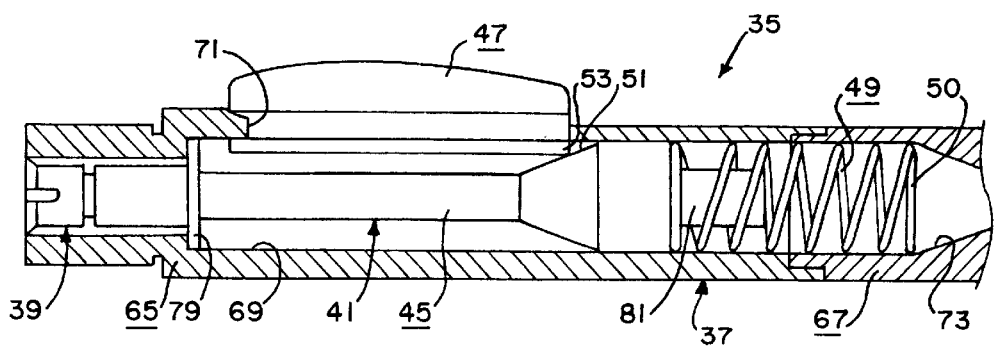
FIG. 11 is an enlarged sectional view of one end of the medical implant insertion instrument shown in FIG. 10.
Figure 12:
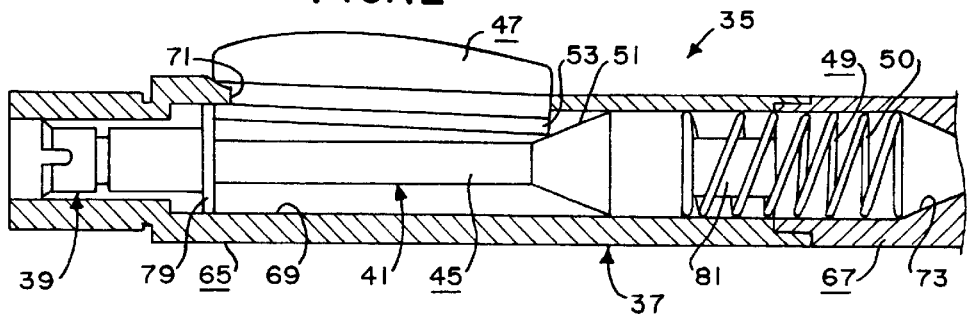
FIG. 12 is a sectional view similar to FIG. 11 but showing certain parts thereof in a moved position.
Figure 13:
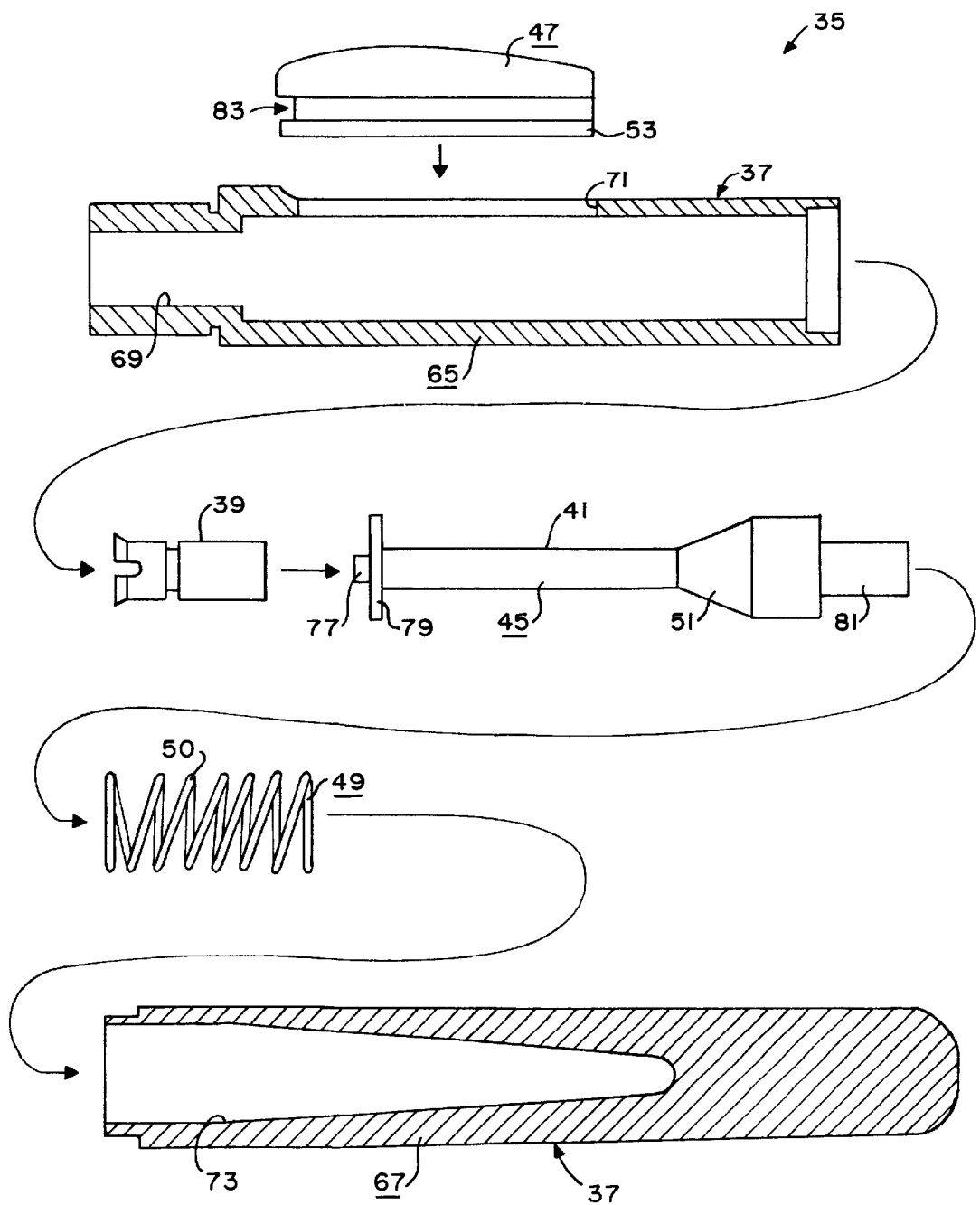
FIG. 13 is an exploded view of the medical implant insertion instrument of the medical implant insertion system of the present invention, with parts thereof shown in section for clarity.

A preferred embodiment of the medical implant insertion system of the present invention is shown in FIGS. 1–15, and identified by the numeral 11. The medical implant insertion system 11 is designed for easy, economical and precise implantation of medical implants 13, and is especially designed for the implantation of punctal occluders (punctum plugs) such as the punctal occluder disclosed in Wallace, U.S. Pat. No. 5,830,171, issued Nov. 3, 1998, incorporated herein by reference. Such a medical implant 13 includes a first end 15, a second end 17, and an aperture 19 extending into the second end 17 (see FIGS. 8 and 9) for receiving the tip of an insertion tool, etc.

The medical implant insertion system 11 includes at least one and preferably a plurality of medical implant cartridges 21. Each medical implant cartridge 21 incudes a medical implant 13, a head 23 having a first end 25 and a second end 27, and a pin 29 having a first end 31 and a second end 33. The pin 29 slidably extends through the head 23 with the first end 31 of the pin 29 being located adjacent the first end 25 of the head 23 and being removably attached to the medical implant 13 and with the second end 33 of the pin 29 being positioned adjacent the second end 27 of the head 23. The second end 33 of the pin 29 preferably has an enlarged portion 34 formed by a collar member or the like.

The medical implant insertion system 11 includes a medical implant insertion instrument 35. The medical implant insertion instrument 35 includes a handle 37 for removable attachment to the second end 27 of the head 23 of the medical implant cartridge 21, collet means 39 for attachment to the second end 33 of the pin 29 of the medical implant cartridge 21 when the handle 37 is attached to the second end 27 of the head 23 of the medical implant cartridge 21, and actuator means 41 for causing the medical implant 13 of the medical implant cartridge 21 to detach from the pin 29 of the medical implant cartridge 21.

At least the medical implant 13 and first end 25 of the head 23 of each of the medical implant cartridges 21 are preferably provided sterile, and a removable cap 43 is preferably provided for protecting the sterile medical implant 13, etc. The cap 43 is preferably a clear disposable member for being snapped over the first end 25 of the head 23 of the medical implant cartridge 21 similar to the removable cap of a fountain pen or the like.

The actuator means 41 preferably includes an actuator body 45 fixedly attached to the collet means 39 so that the collet means 39 will move with the actuator body 45, and an actuator button 47 for causing the actuator body 45 to move from a first or out position to a second or in position. The actuator means 41 also preferably includes an urging means 49, preferably a coil spring 50 or the like, for urging the actuator body 45 to the out position. The actuator body 45 preferably includes a inclined plane portion 51, and the actuator button 47 preferably includes a pusher portion 53 for engaging the inclined plane portion 51 of the actuator body 45 so that downward movement of at least one end of the actuator button 47 will cause the actuator body 45 to move to the in position. A protective pen clip style cover 54 may be provided for snapping over the first end of the handle 37 when then medical implant cartridge 21 is not mounted thereon for protecting the collet means 39, etc., and for allowing the medical implant insertion instrument 35 to be clipped to a physician's pocket similar to a fountain pen or the like.

The actual construction, design and size of the medical implant insertion system 11 may vary as will now be apparent to those skilled in the art. When used for inserting punctal occluders, the medical implant insertion system 11 is preferably substantially the same size and has substantially the same appearance as a typical fountain pen.

The head 23 may be constructed from two basic parts, an elongated cannula 55 and a body 57. The body 57 has a central aperture 59 therethrough sized on the first end so that the second end of the cannula 55 can be pushed thereinto to secure the cannula 55 and body 57 firmly together, and sized on the second end so that the first end of the handle 37 can be snapped thereinto to removably secure the handle 37 and medical implant cartridge 21 together. The cannula 55 and body 57 can, of course, be constructed as an integral, one-piece unit out of plastic or the like. The pin 29 may consist of an elongated metal wire 61 sized so that the first end thereof can be tightly pushed into the aperture 19 in the medical implant 13 to secure the medical implant 13 thereto, and a silicone collar 63 glued or otherwise fixed to the second end of the wire 61 to form the enlarged portion 34 of the second end 33 of the pin 29. To mount the pin 29 to the head 23, the first end 31 of the pin 29 is merely placed into the second end of the aperture 59, shook until it enters the cannula 55, and then pushed through the cannula 55 until the first end 31 of the pin 29 extends past the first end of the cannula 55. The medical implant 13 can then be placed on the first end 31 of the pin 29 and the cap 43 snapped onto the first end 25 of the body 57 of the head 23 over the medical implant 13. The entire medical implant cartridge 21 is sterilized and preferably packaged in a sterile package to allow removal of the sterile medical implant cartridge 21 using a standard "peel and drop" technique. The medical implant cartridge 21 is preferably provided as a tray having ten individually sterile, tear off packages, each including an individually sterile medical implant cartridge 21.

The handle 35 may be constructed in two anodized aluminum parts, a barrel front 65 and a barrel back 67 glued or cemented together during assembly. The barrel front 65 has a central aperture 69 that extends completely therethrough and a slot 71 that opens into the central aperture 69 for receiving the actuator button 47. The first end of the aperture 69 is preferably reduced or stepped down relative to the second end of the aperture 69. The barrel back 67 preferably has a dead end, central aperture 73 that extends rearwardly from the first end thereto.

The collet means 39 may be machined or otherwise formed with a slotted cylindrical first end having a central aperture 75 in at least the first end thereof for receiving the enlarged portion 34 of the pin 29 in a manner to hold the pin 29 to the collet means 39 for movement with the collet means 39. The central aperture 75 preferably extends completely through the collet means 39.

The actuator body 45 may be machined or otherwise formed with a boss 77 on the first end thereof for being inserted into and glued to the second end of the aperture 75 of the collet means 39 to secure the collet means 39 and actuator means 41 together. A flange 79 is preferably provided on the actuator body 45 adjacent the boss 77, and a second boss 81 is provided on the second end of the actuator body 45, with the inclined plane portion 51 located between the flange 79 and boss 81 and with the boss 81 having a cross sectional area smaller that the cross sectional area of the actuator body 45 immediately adjacent the boss 81.

To assemble the handle 37, the boss 77 of the actuator body 45 is inserted into the second end of the aperture 75 in the collet means 39 and the two parts glued together to join the collet means 39 and actuator means 41 together as an integral part. The coil spring 50, etc., is placed into the aperture 73 in the barrel back 67. The collet means 39—actuator means 41 assembly is pushed into the aperture 69 of the barrel front 65 from the second end of the aperture 69. The flange 79 is engage the end of the stepped down portion of the aperture 69 to prevent the collet means 39—actuator means 41 assembly from passing completely through the aperture 69. Next, the barrel 65 and barrel back 67 are pushed together and glued or cemented together, etc., with the boss 81 on the second end of the actuator body 45 extending into the center of the coil spring 50, etc., to align the parts together. The slotted end 83 of the actuator button 47 is then slid into first end of the slot 71 and the rear end of the button 47 is pressed toward into the slot 71 until the button 47 snaps into place on the barrel front 65.

In the preferred manner of using the medical implant insertion system 11, a sterile package containing a sterile medical implant cartridge 21 is opened, using a standard "peel and drop" technique to drop the sterile medical implant cartridge 21 onto the physician's hand. The protective pen clip style cover 54, if used, is removed from the first end of the handle 37, and the second end 27 of the head 23 of the medical implant cartridge 21 is snapped onto the first end of the handle 37. When the second end 27 of the head 23 of the medical implant cartridge 21 is snapped onto the first end of the handle 37, the collar 63 of the pin 29 will extend into the central aperture 75 of the first end of the collet means 39. The removable cap 43 can then be gently removed from the head 23 by being pulled straight out, to expose the sterile medical implant 13 for insertion. The insertion of the medical implant 13 should follow standard or desired medical procedures. For example, in the case of a punctal occluder, dilation of the punctum and the use of topical anesthetic may or may not be required. A drop of ocular lubricant and/or antibiotic drop may be placed on the occluder to help facilitate insertion. The physician should hold the handle 37, using a natural grip, with the intended "trigger-finger" oriented over the actuator button 47. The instrument can then be used to insert the medical implant 13 to the proper position. Only after the implant 13 is in its desired position, the physician smoothly pushes the actuator button 47 to cause the actuator body 45 to move to the in position, and cause the collet means 39 to retract the pin 29 to the in position, separating the medical implant 13 from the pin 29, etc. Care should be taken not to prematurely push the actuator button 47 and prematurely release the implant 13. After insertion, the insertion site should be carefully inspected to confirm that the implant 13 has been properly placed. If adjustment is necessary, the use of forceps or a small dilator may be helpful. The remainder of the used medical implant cartridge 21 can then been pulled from the handle 37 and discarded, leaving the medical implant insertion instrument 35 for re-use.

Although the present invention has been described and illustrated with respect to a preferred embodiment and a preferred use therefor, it is not to be so limited since modifications and changes can be made therein which are within the full intended scope of the invention.

What is claimed is:

1. A medical implant insertion system comprising:
   (a) a medical implant cartridge including:
      a medical implant,
      a head having a first end and a second end, and
      a pin slidably extending through said head, said pin having a first end and a second end, said first end of said pin being located adjacent said first end of said head and being removably attached to said medical implant; said second end of said pin being positioned adjacent said second end of said head; and
   (b) a medical implant insertion instrument including:
      a handle for removable attachment to said second end of said head of said medical implant cartridge,
      collet means for attachment to said second end of said pin of said medical implant cartridge when said handle is attached to said second end of said head of said medical implant cartridge, and
      actuator means for causing said medical implant of the medical implant cartridge to detach from said pin of said medical implant cartridge.

2. The medical implant insertion system of claim 1 in which said medical implant cartridge is sterile.

3. The medical implant insertion system of claim 2 in which said medical implant of said medical implant cartridge includes a removable cap for protecting said medical implant.

4. The medical implant insertion system of claim 3 in which is included a plurality of said medical implant cartridges.

5. The medical implant insertion system of claim 1 in which said actuator means of said medical implant insertion instrument includes an actuator body fixedly attached to said collet means so that said collet means will move with said actuator body; and in which said actuator means of said medical implant insertion instrument includes an actuator button for causing said actuator body to move from an out position and to an in position.

6. The medical implant insertion system of claim 5 in which said actuator means of said medical implant insertion instrument includes an urging means for urging said actuator body to said out position.

7. The medical implant insertion system of claim 5 in which said actuator body includes an inclined plane portion; and in which said actuator button includes a pusher portion for engaging said inclined plane portion of said actuator body so that downward movement of said actuator button will cause said actuator body to move to said in position.

8. The medical implant insertion system of claim 1 in which said second end of said pin of said medical implant cartridge has an enlarged portion for receipt by said collet means of said medical implant insertion instrument.

9. The medical implant insertion system of claim 8 in which said enlarged portion of said pin of said medical implant cartridge includes a collar member.

10. A medical implant insertion system comprising:
(a) a plurality of sterile medical implant cartridges, each of said sterile medical implant cartridges including:
a sterile medical implant,
a head having a first end and a second end,
a pin slidably extending through said head, said pin having a first end and a second end, said first end of said pin being located adjacent said first end of said head and being removably attached to said medical implant; said second end of said pin being positioned adjacent said second end of said head, and
a removable cap for protecting said sterile medical implant; and
(b) a medical implant insertion instrument including:
a handle for removable attachment to said second end of said head of one of said medical implant cartridges,
collet means for attachment to said second end of said pin of said one of said medical implant cartridges when said handle is attached to said second end of said head of said medical implant cartridge, and
actuator means for causing said medical implant to detach from said pin of said one of said medical implant cartridges; said actuator means including an actuator body fixedly attached to said collet means so that said collet means will move with said actuator body, an actuator button for causing said actuator body to move from a out position and to an in position, and a spring member urging said actuator body to said out position.

11. The medical implant insertion system of claim 10 in which said actuator body includes an inclined plane portion; and in which said actuator button includes a pusher portion for engaging said inclined plane portion of said actuator body so that downward movement of said actuator button will cause said actuator body to move to said in position.

\* \* \* \* \*